(12) United States Patent
Daffer

(10) Patent No.: US 10,744,340 B2
(45) Date of Patent: *Aug. 18, 2020

(54) CAPSULE WITH WHOLE BODY LED PHOTO-THERAPY

(71) Applicant: Visibelle Derma Institute, Inc., Bloomington, MN (US)

(72) Inventor: Steven J. Daffer, Edina, MN (US)

(73) Assignee: Visibelle Derma Institute, Inc., Bloomington, MN (US)

( * ) Notice: Subject to any disclaimer, the term of this patent is extended or adjusted under 35 U.S.C. 154(b) by 361 days.

This patent is subject to a terminal disclaimer.

(21) Appl. No.: 15/796,141

(22) Filed: Oct. 27, 2017

(65) Prior Publication Data

US 2018/0043176 A1 Feb. 15, 2018

Related U.S. Application Data

(63) Continuation of application No. 12/396,847, filed on Mar. 3, 2009, now Pat. No. 9,808,644.

(60) Provisional application No. 61/033,122, filed on Mar. 3, 2008.

(51) Int. Cl.
*A61N 5/06* (2006.01)
*A61H 33/06* (2006.01)

(52) U.S. Cl.
CPC ......... *A61N 5/0613* (2013.01); *A61H 33/067* (2013.01); *A61H 2201/10* (2013.01); *A61H 2203/0443* (2013.01); *A61N 5/0616* (2013.01); *A61N 5/0617* (2013.01); *A61N 5/0618* (2013.01); *A61N 2005/0626* (2013.01); *A61N 2005/0637* (2013.01); *A61N 2005/0652* (2013.01); *A61N 2005/0659* (2013.01); *A61N 2005/0662* (2013.01); *A61N 2005/0668* (2013.01)

(58) Field of Classification Search
CPC ........................................................ A61N 5/06
USPC .................................... 606/2–19; 607/88–94
See application file for complete search history.

(56) References Cited

U.S. PATENT DOCUMENTS

| 1,221,163 | A | 4/1917 | Frink |
| 1,643,528 | A | 9/1927 | Thurston |
| 1,797,916 | A | 3/1931 | Kruse |
| 2,012,221 | A | 8/1935 | Clark et al. |
| 2,096,128 | A | 10/1937 | Mortrude, Jr. |
| 2,240,819 | A | 5/1941 | Waly |
| 2,300,455 | A | 11/1942 | Lukats |
| 2,567,614 | A | 9/1951 | Merriam |
| D189,951 | S | 3/1961 | Cosper |
| 3,409,915 | A | 11/1968 | Jauvais |
| 3,772,713 | A | 11/1973 | Roullier |
| 3,945,058 | A | 3/1976 | Gardner |

(Continued)

FOREIGN PATENT DOCUMENTS

| DE | 725804 | 3/1944 |
| DE | 3915008 A1 | 11/1990 |

(Continued)

*Primary Examiner* — Lynsey C Eiseman
(74) *Attorney, Agent, or Firm* — Westman, Champlin & Koehler, P.A.

(57) ABSTRACT

A personal therapy compartment includes a base of size to receive a human patient. The compartment includes a bed in the base said bed being made of a light transmissive material. An array of lights mounted is below the bed to transmit light onto a body supported on the bed. A control panel controls at least the wavelength, intensity and pulsation of the light.

16 Claims, 5 Drawing Sheets

(56) References Cited

U.S. PATENT DOCUMENTS

| | | |
|---|---|---|
| 4,031,573 A | 6/1977 | Romanoff |
| 4,055,863 A | 11/1977 | Duval |
| D249,894 S | 10/1978 | Brancaccio et al. |
| 4,130,120 A | 12/1978 | Kohler, Jr. |
| D255,491 S | 6/1980 | Brancaccio et al. |
| 4,258,706 A | 3/1981 | Shank |
| 4,277,855 A | 7/1981 | Poss |
| D275,605 S | 9/1984 | Taylor |
| 4,565,188 A | 1/1986 | Hardie |
| 4,671,284 A | 6/1987 | Wilson et al. |
| 4,712,538 A | 12/1987 | Hardie et al. |
| D297,863 S | 9/1988 | Hardie et al. |
| 4,833,739 A | 5/1989 | Sakakibara et al. |
| 4,862,526 A | 9/1989 | Berger |
| 4,884,574 A | 12/1989 | Hardie et al. |
| D317,650 S | 6/1991 | Soder |
| 5,101,809 A | 4/1992 | Daffer et al. |
| D326,720 S | 6/1992 | Garrison et al. |
| 5,228,150 A | 7/1993 | Parker |
| 5,255,399 A | 10/1993 | Park |
| D340,992 S | 11/1993 | Garrison |
| 5,416,931 A | 5/1995 | Wolfenden et al. |
| D360,469 S | 7/1995 | Panelli et al. |
| 5,441,529 A | 8/1995 | Dorsch |
| 5,511,254 A | 4/1996 | O'Brien |
| 5,546,678 A | 8/1996 | Dhaemers |
| D377,530 S | 1/1997 | Daffer et al. |
| 5,645,578 A | 7/1997 | Daffer et al. |
| D384,416 S | 9/1997 | Daffer et al. |
| 5,891,186 A | 4/1999 | Daffer et al. |
| D413,388 S | 8/1999 | Daffer et al. |
| 6,004,344 A | 12/1999 | Fujii |
| D453,834 S | 2/2002 | Daffer et al. |
| 6,350,275 B1 | 2/2002 | Vreman et al. |
| 6,497,717 B1 | 12/2002 | Daffer et al. |
| 6,623,511 B1 | 9/2003 | Daffer et al. |
| 7,282,060 B2 | 10/2007 | Debenedictis et al. |
| 7,526,344 B2 | 4/2009 | Kim |
| 2002/0198575 A1 | 12/2002 | Sullivan |
| 2006/0200211 A1 | 9/2006 | Lin |
| 2006/0253175 A1 | 11/2006 | Fan et al. |
| 2007/0282400 A1 | 12/2007 | Gorham |
| 2010/0049282 A1 | 2/2010 | Wang |
| 2010/0063487 A1 | 3/2010 | Straalen |

FOREIGN PATENT DOCUMENTS

| | | |
|---|---|---|
| EP | 0986985 A1 | 3/2000 |
| FR | 2086905 A5 | 12/1971 |
| FR | 2629343 A1 | 10/1989 |
| FR | 2803512 A1 | 7/2001 |
| GB | 1490381 | 11/1977 |
| JP | 8112302 A | 5/1996 |
| JP | 11114008 A | 4/1999 |
| WO | 0002491 A1 | 1/2000 |
| WO | 03034971 A2 | 5/2003 |

CAPSULE WITH WHOLE BODY LED PHOTO-THERAPY

CROSS REFERENCE TO RELATED APPLICATION(S)

This application is a continuation of U.S. patent application Ser. No. 12/396,847, filed Mar. 3, 2009, which claims priority of U.S. Provisional Patent Application Ser. No. 61/033,122 which was filed on Mar. 3, 2008, the contents of which is incorporated by reference in its entirety.

FIELD OF THE INVENTION

The present invention relates to an individual covered compartment or capsule in which a person can lie for various therapeutic treatments. The capsule includes the ability to provide for a whole body photo-therapy system including controllable wavelength LEDs and/or infrared lights.

BACKGROUND OF THE INVENTION

In the prior art, various environmental capsules have been advanced, including for example, the structure shown in U.S. Pat. Nos. 5,101,809 and 6,497,717. The treatments that are present in the prior art devices include steam therapy, heat therapy, infrared heat and light exposure, pleasing sound sources, aroma therapy and some capsules provide a shower mounted in the cover or base of the capsule.

The capsules generally comprise a base that is large enough to accommodate a support or bed in a lower portion, and a hinged cover that can be opened so that a person can get in and out of the lower part or base of the capsule. The cover usually has individual controls for the provided therapy source such as a shower, heat, steam, sound, aroma or other therapy source can be mounted in a position where a person lying on the bed can reach and operate the controls. In addition, it has long been known to have a vibrator on the bed to provide a relaxing, massage type vibration.

SUMMARY OF THE INVENTION

The present invention comprises a personal therapy capsule that can incorporate one or more of the features from the prior art. The capsule of the present invention further includes an array of LED lights and/or infrared lights mounted below a transparent bed or body support that will support a human lying generally horizontally. Additionally, LED lights have desired hue or color and infrared lights can be mounted directly in the cover and arranged along the length of the cover and the width of the cover so that a total body photo therapy treatment can be advanced.

The present invention has LEDs and infrared lights that have controllable wavelength output. The wavelength can be adjusted through known controls from between approximately 400 nm to 800 nm in the visible spectrum and the infrared range is between 800-2000 nm.

Each individual condition of a person can be treated or provided with therapy at a different wavelength, for example, 400 nm, 560 nm or 640 nm, etc. to provide therapy for conditions including, but not limited to, psoriasis, dermatological conditions, skin tightening, circulatory stimulation, fine lines and wrinkles, obesity and excessive weight, stimulation for hair growth, reducing swelling and hematoma, accelerating wound healing, enhancing tissue repair, relieving inflammation and pain associated with inflammation, relieving neurogenic pain, reversing effects of toxins in the body, regenerating nerves, increasing fibroblast and collagen growth factors and the treatment of arthritis and carpal tunnel syndrome.

The device can utilize selected visible wavelength lights such as colorful LEDs that are selected in the known blue, red, yellow and green hues, and selected thermal generation invisible infrared lights. The device allows the selected visible and the selected invisible lights to be utilized at desired frequencies, together or independently, to treat a symptom. For instance, wrinkles are typically treated with 630 nm visible light and carpal tunnel syndrome is typically treated with invisible light at a wavelength of about 830 nm.

The LED and/or infrared light therapy is available to the entire body trunk or to regions of the body trunk, such as the shoulders, back, mid-section, stomach and chest. The LED and/or infrared light therapy is available to the limbs including the right leg and/or left leg and the right and or left arm. Any combination of areas of the body can be treated by having the lights arrayed in clusters or "gangs" that can be controlled individually. The lights also can be timed, pulsed, and varied in intensity, such as with the power level.

The display for the user or patient can be a LCD display that will show which sections are energized, and at what wavelength, as well as other critical information as to the interior temperature, and similar parameters.

DETAILED DESCRIPTION OF THE PREFERRED EMBODIMENTS

Figure 1:
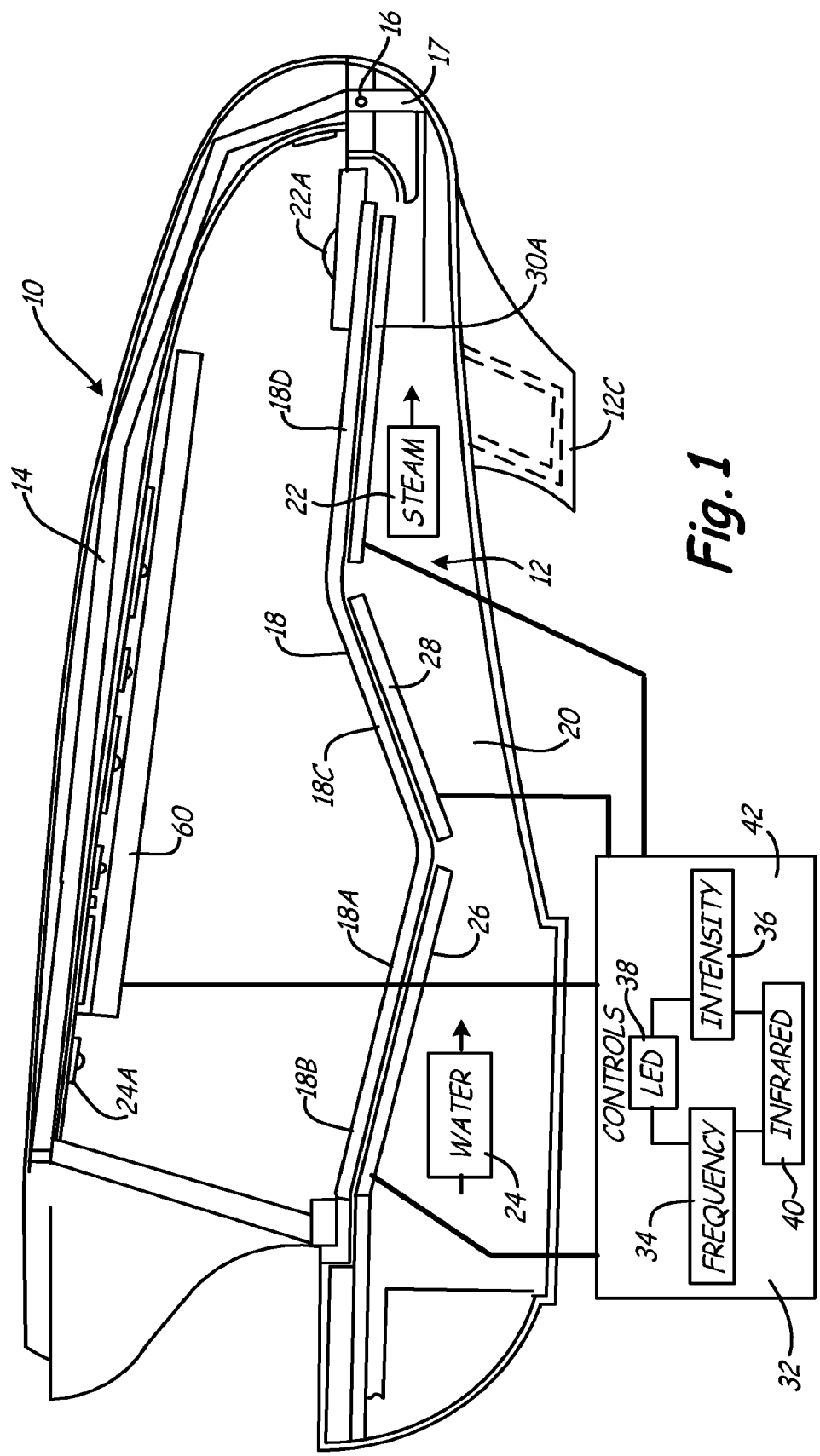
FIG. 1 is a schematic sectional view of a personal treatment capsule with a cover in a closed position.

Referring to FIG. 1, a full body photo treatment compartment assembly is generated at 10 in cross-section, to show the interior. The system includes a base unit 12, and a cover 14 that is hinged at a hinge axis 16 at the foot end 17 of the compartment base 12. The base 12 is supported on a three-point leg system, preferably including a pedestal 12A, and forward legs 12C.

The three-legged arrangement provides stability of support without rocking or problems with unevenness of a support floor. Other forms of support for the base can be utilized and are contemplated.

The base 12 is provided with a bed platform 18, in this case made out of a clear acrylic or other clear plastic material, so that it is transparent to light of different wavelengths. The upper surface 18A of the bed positioned at various angles and the bed 18 includes an upper body portion 18B that supports the shoulder and upper back region of a person lying on the support bed 18. The bed 18 also includes a lower back panel or portion 18C, that is at a comfortable angle relative to the portion 18B, and a leg panel or support 18D that is at the foot end of the bed.

The base 12 forms a lower compartment 20 that can house various components, such as a steam generator 22 that is mounted to provide for steam therapy, if desired, at steam outlets represented generally at 22A. The compartment 20 also can hold a water tank 24 that will have a pump and supply lines connected to showerheads. By way of example, a showerhead 24A is shown in the cover 14 in FIG. 1. The showing of the shower head is not limited to any particular placement. If desired, showerheads can be placed in other locations along the sides of the cover or in the base. Suitable drainage troughs will be provided and this can easily be done because the base 12 is generally molded plastic or fiberglass material that can be shaped as desired.

Figure 3:
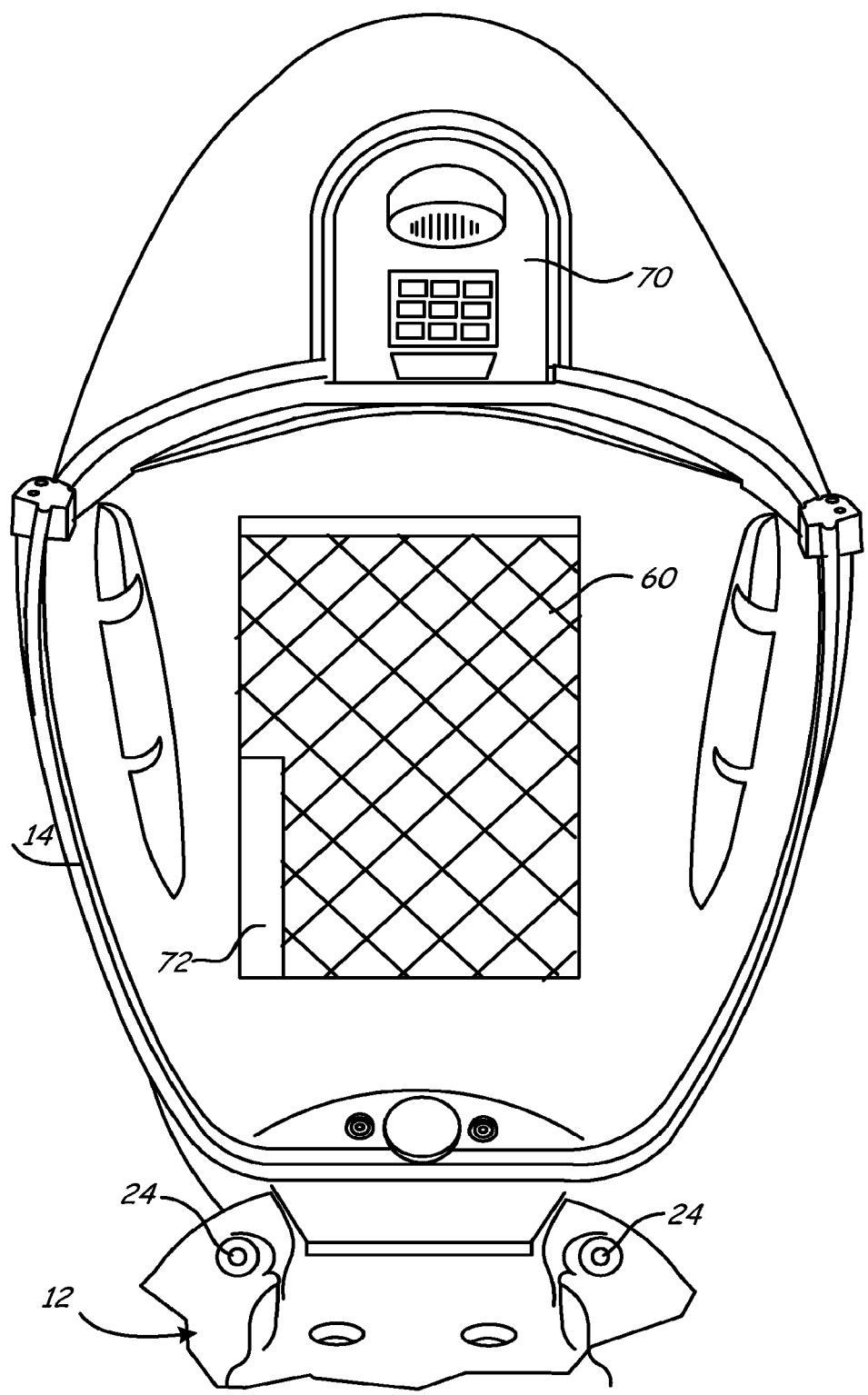
FIG. 3 is a view of a cover of the capsule of FIG. 1 in an open position showing a lighting array on the interior of the cover.

The present invention utilizes the transparent bed 18 on which a person can lie, in connection with LED lights and infrared light sources comprising small bulbs mounted in an array on a light support panel 26 for the upper back portion of the bed. A light support panel 28 is provided for the lower back, immediately below the lower back panel 18C of the bed, and a pair of leg light panels 30A and 30B are provided (see FIG. 3) that are individually controlled so that one leg or the other or both can be provided with light therapy through the transparent bed which is represented in FIG. 3 by the outline.

The light support panels 28, 30A and 30B are illustrated being mounted to the bed 18. However, the light support panels 28, 30A and 30B can also be mounted the wall of the lower compartment 20. When mounted to the wall of the lower compartment 20, the clusters light support panels 28, 30A and 30B are less likely to be damaged when compared to mounting the light support panels to the bed 18. Also when the panels 28, 30A and 30B are mounted to the wall of the lower compartment 20, the bed can be easily removed and cleaned and/or sanitized.

The light panels 26, 28, 30A and 30B can be seen below the bed 12 because the bed is transparent, and the grid pattern shown represents a multitude of small LED lights that are mounted in the panels 26, 28, 30A and 30B. The numbers of the LEDs that are used, and the colors that are used can be varied as desired by the operator, and can be blue, red, yellow, green, clear, or other colored light sources that can be controlled as to intensity and as to the frequency of the output. The controls indicated in 32 are conventional controls. The block 38 represents the individual LED arrays, and block 40 represents the infrared arrays. Each LED or infrared array of lights can be selected and switched for controlling the selected array. The location of the array will be displayed on the operator's screen. The controls are available for modifying the frequency of the lights of the selected array at block 38 as are represented at block 36. As can be seen, the control block 42 houses these various electronic components and then the light panels 26, 28, 30A and 30B are selectively, or simultaneously connected through suitable lines to the controls. An operator display at a location 66 can have the needed information displayed to the user.

Besides being able to control the wavelength of the LED array, the control panel can also be utilized to control the energy output of the light arrays. A typical energy output for the LED used in the LED arrays range from about 5 mW to about 5 W from each LED in the array. Another typical energy output is between 5 mW and 500 mW from each LED in the array. The control panel is also able to control the angle at which the beams of light engage the person where the LED beam angle typically ranges from 0 to 90 degrees.

In FIG. 3, the darker outlines represent placement of infrared light arrays for heat therapy along the shoulders, as indicated at 46A and 46B, and along the buttock or back portions at 48A and 48B, as well as the myriad of LEDs forming arrays represented by the lines forming squares in the panels 26, 28, 30A and 30B.

The placement of the light panels can be as desired, and can include a central infrared section on both of the panels 26 and 28 as indicated at 50A and 50B.

In the person's leg area, infrared light sections are shown at 52A and 52B, and again these can be controlled from the controls 42 using suitable electronic controls available for lights.

Schematically represented at 54 are brackets for holding the bed panel 18 in position relative to the base 12. These mounts can be of any desired type.

Figure 4:
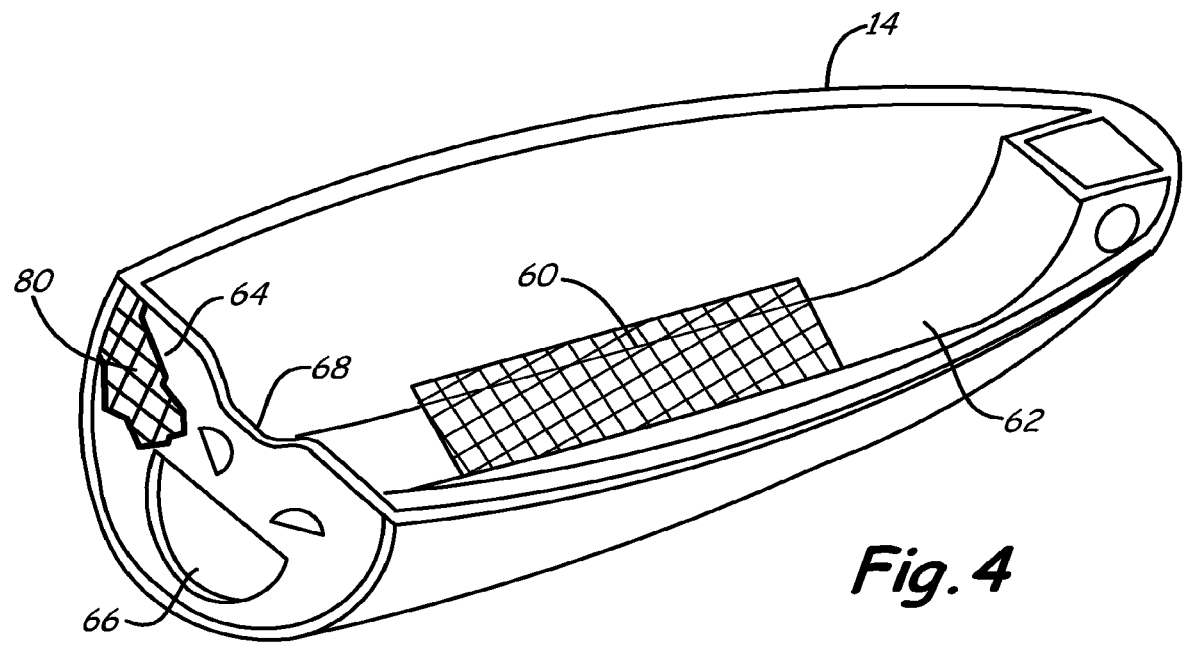
FIG. 4 is a schematic plan view of the interior of the cover with the cover inverted.
Figure 5:
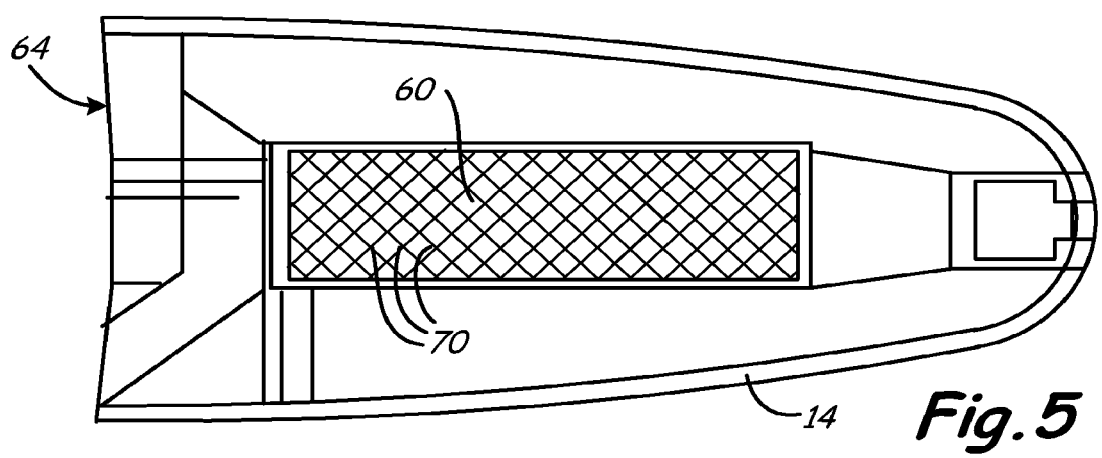
FIG. 5 is a perspective view of the cover shown inverted with a location of a control panel for an operator and location of control regions shown at the head end of the cover.

The cover 14 is shown in FIG. 1 as supporting not only showerheads 24A but a light panel assembly 60 that is supported on the upper portions of the cover in a suitable manner, and which contains a myriad of LEDs or infrared lights forming light arrays. FIGS. 4 and 5 illustrate the cover 14 in an inverted position. FIG. 4 is a perspective view showing the LED panel 60 in position along a tunnel member 62 that can be for carrying heated air if desired. The cover 14 has a dividing panel 64 at the head end, and this includes the region 66 for supporting the control panel display for the controls shown schematically at 42. The panel 64 is recessed as at 68 to permit the neck of the person lying in the compartment to cross the panel 64 so the person's head is to the exterior of the closed compartment.

FIG. 5 is a top plan view to show an array 60 of LEDs or other lights, and it can be seen at the length and width that the LED panel can be made as desired and then supported on the interior top of the cover 14.

Each of the line intersections shown in the gridwork and indicated at 70 represents an LED. The number of LEDs can be varied substantially as desired to suit the treatment purposes.

Figure 2:
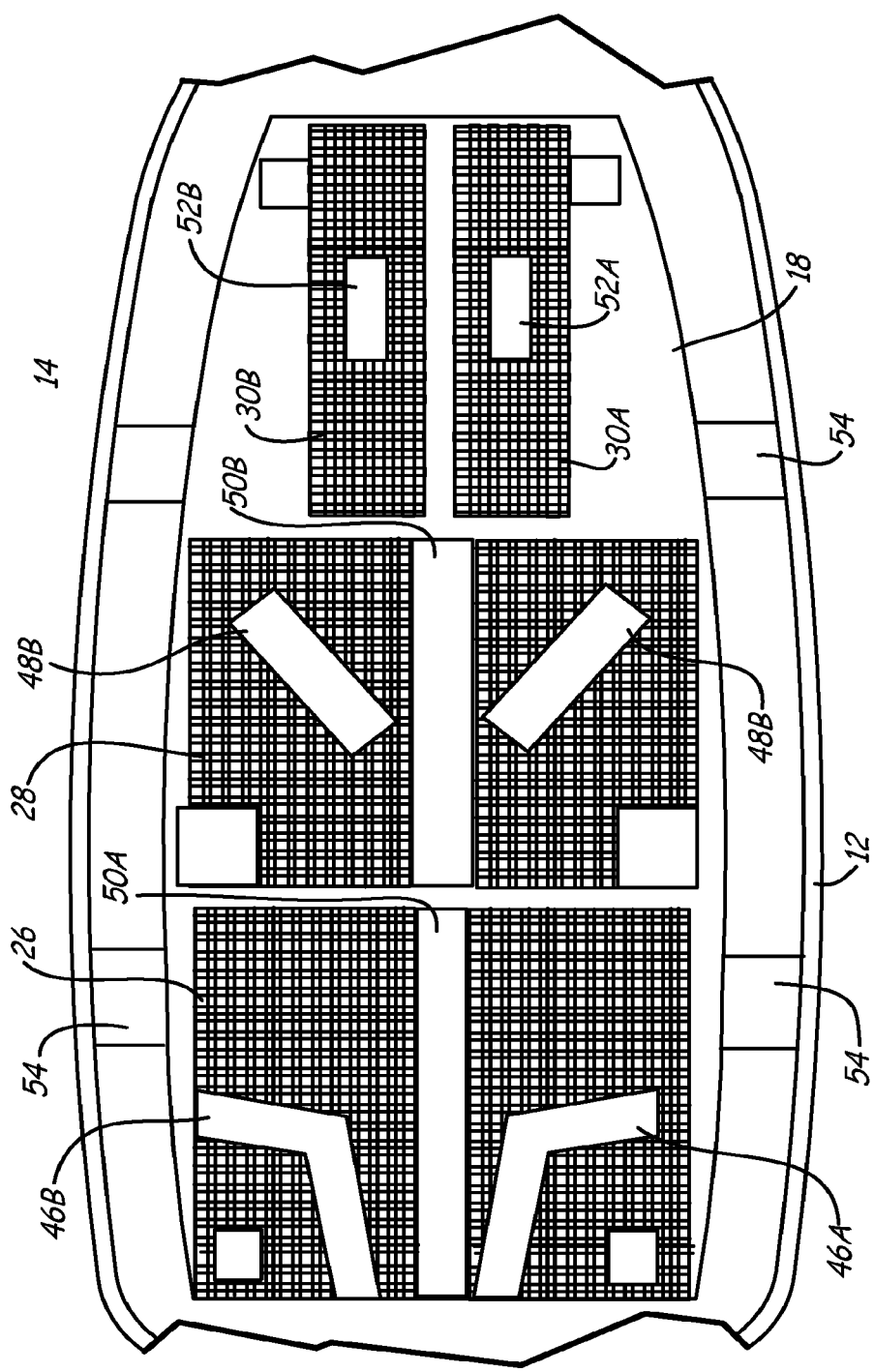
FIG. 2 is a planned view of the bed of FIG. 1 schematically showing a layout of lighting arrays.

In FIG. 2, the LED or light array panel 60 is illustrated with the cover 14 open, and the control panel is illustrated at 70, and is of a different form that can be folded up or down into the cover, as desired.

Steam outlets 24A are illustrated at the forward end of the unit and these can be placed at any desired location.

In FIG. 2, the LED grid is shown schematically, but additionally a panel indicated at 72 can be provided for an array of infrared lights at desired locations along the panel 60, and as shown, the array of infrared lights can be separately controlled by the control system.

Although LED grids are illustrated, it is also contemplated to utilize smaller sized clusters where more clusters are utilized for one large grid. The clusters are typically of the same configuration and size such that when a cluster malfunctions, only one cluster needs to be replaced instead of an entire array. While the entire array must be replaced, only a small portion of the array may have malfunctioned. Therefore, by providing numerous clusters of the same configuration, such as a substantially round perimeter, maintenance time and replacement costs can be reduced when compared to the large arrays.

A cluster of lights can have any desired number of LEDs. A cluster typically includes between 1,000 and 20,000 LEDs.

By operating the controls to provide for different wavelengths of light from the LEDs, for example 400 nm, 560 nm, 640 nm, or greater, the photo-therapy can be directed toward a specific type of treatment, such as for psoriasis, dermatological conditions, skin tightening, circulatory stimulation, fine lines and wrinkles, obesity and excessive weight, stimulation for hair growth, reducing swelling and hematoma, accelerating wound healing, enhancing tissue repair, relieving inflammation and pain associated with inflammation, relieving neurogenic pain, reversing effects of toxins in the body, regenerating nerves, increasing fibroblast and collagen growth factors and the treatment of arthritis and carpal tunnel syndrome. For example, the bed, with the 3 LED panels, can have an array in the range of 8,000 or more yellow, blue, green or red LEDs, and also an array of about 2,000 bulbs that emit infrared wavelengths for heat.

A person will lie on the bed 18 to receive the phototherapy as light is transmitted through the clear bed 18.

The controls can be provided for continuous or variable pulsation frequency of the light, and the intensity, power level, the infrared thermal temperature, and intermixing the sequence of LED and infrared treatment can be made. Also, oxygen can be injected into the capsule to raise the oxygen concentration within the capsule.

The water tank 24 can be used for providing a humidifying vaporization and/or misting system through the outlets shown at 24A, that would allow the application and spray or envelopment of the body of the user of different solutions that are photosensitive and/or photoactive for different therapies. Photosensitive agents can be placed in the tank 24 and then misted onto the body of a person on the bed at desired times.

Figure 6:
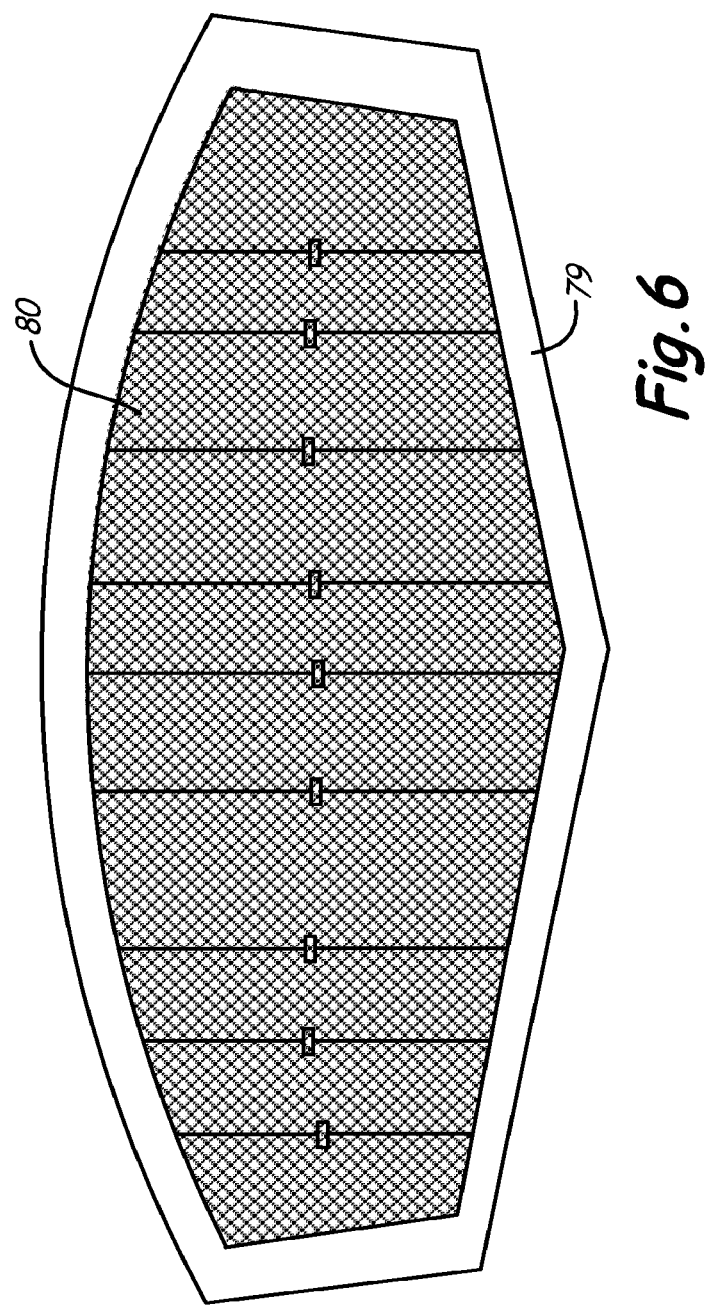
FIG. 6 is a flat layout of an LED array for placing adjacent a face of a patient in the capsule.

FIG. 6 illustrates a schematic view of a facial panel 79 that supports an array of a number of LEDs and is indicated at 80. This facial panel 79 can be suspended on or adjacent the divider panel 64 on the cover, and provides for the panel shown at 80 is fragmentarily shown in FIG. 4. The panel 79 and light array 80 can be made to cover substantially the entire area or selected portions of the panel 64 and can be independently suspended and located, if desired. The facial panel 79 can also include adjustable LEDs, of various colors as outlined, and can include infrared lights as well.

The infrared light sources can be small bulbs arranged in an array, or larger forms as desired.

Features such as dry heat air, steam, ceramic and/or course midrange and far-range infrared heaters can be added in the cover as previously shown in the prior art, and a mist source, a shower, a humidifier, a hydrotherapy source, electrical stimulation and various entertainment sources can be used, such as DVD players, music sources and the like.

Although the present invention has been described with reference to preferred embodiments, workers skilled in the art will recognize that changes may be made in form and detail without departing from the spirit and scope of the invention.

What is claimed is:

1. A personal therapy compartment comprising:
   a base extending from a first end to a second end, wherein the base is of size to receive a human being wherein the base includes a base surface,
   a bed supported by and separated from the base surface of the base, said bed having an upper surface and a lower surface and being made of a light transmissive material and wherein the lower surface of the bed and the base surface are spaced apart from each other,
   at least two spaced apart bed arrays of light emitting diodes located between the lower surface of the bed and the base surface of the base wherein each bed array of light emitting diodes is adapted to transmit visible light through the bed and onto a body of the human being supported on the bed,
   a cover pivotally attached to the base proximate the first end and wherein the cover comprises:
   a divider panel positioned proximate the second end of the cover, wherein the divider panel is configured to be positioned about a neck of the human to provide different environments for the human's body and the human's head;
   a facial array supported by the divider panel, wherein the facial array comprises one or more light emitting diodes configured to emit light towards a face of the human; and
   a control panel configured to control one or more selected array of light emitting diodes of the at least two spaced apart bed arrays and the facial array, wherein the control panel is configured to control at least intensity and duration of beams of light emitted from the selected array of light emitting diodes such that the beams of light are transmitted onto a person laying on the upper surface of the bed.

2. The compartment of claim 1, wherein least two spaced apart bed arrays of light emitting diodes are selected from one or more of the colors consisting of red, blue, yellow, and green.

3. The compartment of claim 1, wherein said at least two array of light emitting diodes comprises a plurality of arrays wherein each array is mounted on a panel secured below selected sections of the light-transmissive bed, the light array on each of said panels being individually controllable as to light intensity, frequency and angle at which the beams of light engage the person laying on the upper surface of the bed with the control panel.

4. The compartment of claim 1, and further comprising a light-transmitting source supported by the cover, the light-transmitting source configured to direct light toward the person when the cover is lowered, the light-transmitting source coupled to the control panel wherein the control panel is configured to cause the light-transmitting source to direct light at selected frequencies and intensities over a substantial portion of a body of a person lying on the bed.

5. The compartment of claim 1 and wherein the at least two arrays of light emitting diodes comprises LED bulbs each having an energy output intensity of between 5 mW and 5 W.

6. The compartment of claim 4 and wherein the light-transmitting source supported by the cover comprises an array of LED bulb wherein each LED bulb has an intensity of between 5 mW and 500 mW.

7. The compartment of claim 1 and wherein the light is pulsed.

8. The compartment of claim 1 and an engagement angle of the light of the LED bulb ranges between 0 degrees and 90 degrees relative to the person laying on the bed.

9. The compartment of claim 1 and wherein the controller is configured to manipulate the at least two arrays of light emitting diodes such that the light is transmitted in the visible spectrum between 400 nm and 800 nm.

10. The compartment of claim 1 and further comprising at least a third light source configured to transmit light onto the body in the infrared frequency range of between 800 nm and 2000 nm.

11. The compartment of claim 1 and wherein the array of lights comprises a polygonal perimeter.

12. A personal therapy compartment comprising:
    a base of size to receive a human being wherein the base includes a base surface, a bed supported by and separated a selected distance from the base surface, said bed being made of a light transmissive material and having an upper surface and a lower surface, at least two base arrays, each array comprising light emitting diodes and infrared bulbs within the compartment and positioned between the lower surface of the bed and the base surface of the base, wherein the light emitting diodes are configured to transmit visible light through the bed and onto a body of the human being supported on the bed and the infrared bulbs are configured to transmit infrared light through the bed and onto the body of the human being supported on the bed wherein the infrared light provides thermal energy, a cover pivotally attached to the base proximate the first end and wherein the cover comprises:

a divider panel positioned proximate the second end pf the cover, wherein the divider panel is configured to be positioned about a neck of the human to provide different environments for the human's body and the human's head;

a facial array supported by the divider panel, wherein the facial array comprises a plurality of light emitting diodes configured to emit light towards a face of the human; and a control panel configured to control parameters of one or more selected arrays including the at least two base arrays and the facial array, wherein the parameters that are controlled include wavelength, duration and intensity.

13. The compartment of claim 12, wherein said at least two base arrays are mounted on a plurality of panels below selected sections of the light-transmissive bed, a base light array on each of said panels being individually controllable as to light intensity and frequency.

14. The compartment of claim 12, and further comprising a light-transmitting source supported by the cover, the light-transmitting source configured to direct light toward the person when the cover is lowered, the light-transmitting source coupled to the control panel wherein the control panel is configured to cause the light-transmitting source to direct light at selected frequencies and intensities over a substantial portion of a body of a person lying on the bed.

15. A personal therapy compartment comprising:

a base having an inner cavity defined by a base surface wherein the cavity is of a size to receive a body of a human being and wherein the base includes a front end and a distal end;

a bed extending from proximate the distal end of the base to proximate the front end and wherein the bed is supported proximate the front end and the back end of the base such that the bed is a distance from the base surface wherein the bed is of a light transmissive material, wherein the bed includes an upper surface and a lower surface; and a plurality of spaced apart base arrays of light emitting diodes and infrared bulbs located between the bottom surface of the bed and the base surface wherein each base array of light emitting diodes and infrared bulbs; and a cover pivotally attached to the base proximate the first end and wherein the cover comprises:

a divider panel positioned proximate the second end of the cover, wherein the divider panel is configured to be positioned about a neck of the human to provide different environments for the human's body and the human's head; and a facial array secured to the divider panel, wherein the divider panel comprises a plurality of light emitting diodes configured to emit light towards a face of the human wherein the control panel is configured to control at least a wavelength of the facial array; and a control panel in communication with each base array of the plurality of spaced apart arrays and the facial panel wherein the control panel is configured to adjust at least a wavelength of the light emitted by the light emitting diodes in the visible light spectrum and the infrared light emitted by the infrared bulbs, intensity, thermal temperature and/or pulsation such that the visible light and infrared light transmits through the bed and onto the body of the human being and the face of the human being.

16. The compartment of claim 15 and further comprising:

a light-transmitting source supported by the cover, the light-transmitting source configured to direct light toward the person when the cover is lowered, the light-transmitting source coupled to the control panel wherein the control panel is configured to cause the light-transmitting source to direct light at selected frequencies and intensities over a substantial portion of a body of a person lying on the bed.

\* \* \* \* \*